US011642162B2

(12) United States Patent
Betsugi et al.

(10) Patent No.: US 11,642,162 B2
(45) Date of Patent: May 9, 2023

(54) SURGICAL INSTRUMENT

(71) Applicant: MEDICAROID CORPORATION, Kobe (JP)

(72) Inventors: Shota Betsugi, Kobe (JP); Yu Usuki, Kobe (JP); Kenji Ago, Kobe (JP)

(73) Assignee: MEDICAROID CORPORATION, Kobe (JP)

( * ) Notice: Subject to any disclaimer, the term of this patent is extended or adjusted under 35 U.S.C. 154(b) by 364 days.

(21) Appl. No.: 17/070,923

(22) Filed: Oct. 15, 2020

(65) Prior Publication Data
US 2021/0121223 A1    Apr. 29, 2021

(30) Foreign Application Priority Data

Oct. 23, 2019    (JP) .............................. JP2019-192618

(51) Int. Cl.
| | | |
|---|---|---|
| *A61B 34/30* | (2016.01) | |
| *A61B 18/14* | (2006.01) | |
| *A61B 17/29* | (2006.01) | |
| *A61B 34/00* | (2016.01) | |
| *A61B 46/10* | (2016.01) | |
| *A61B 17/34* | (2006.01) | |
| *A61B 17/00* | (2006.01) | |
| *A61B 18/00* | (2006.01) | |

(52) U.S. Cl.
CPC .............. *A61B 18/14* (2013.01); *A61B 17/29* (2013.01); *A61B 34/30* (2016.02); *A61B 17/3421* (2013.01); *A61B 34/25* (2016.02); *A61B 46/10* (2016.02); *A61B 2017/00526* (2013.01); *A61B 2017/00862* (2013.01); *A61B 2017/2903* (2013.01); *A61B 2018/00083* (2013.01); *A61B 2018/00589* (2013.01); *A61B 2018/00601* (2013.01); *A61B 2018/00767* (2013.01); *A61B 2018/00988* (2013.01); *A61B 2018/1412* (2013.01); *A61B 2034/301* (2016.02); *A61B 2217/007* (2013.01); *A61B 2218/002* (2013.01)

(58) Field of Classification Search
CPC ..... A61B 17/29; A61B 17/3421; A61B 18/14; A61B 2017/00477; A61B 2017/00526; A61B 2017/00862; A61B 2017/00929; A61B 2017/2903; A61B 2018/00083; A61B 2018/00172; A61B 2018/00178; A61B 2018/00589; A61B 2018/00601; A61B 2018/00767; A61B 2018/00988; A61B 2018/1412; A61B 2034/301; A61B 2090/0803; A61B 34/25; A61B 34/30; A61B 34/37

See application file for complete search history.

(56) References Cited

U.S. PATENT DOCUMENTS

8,241,271 B2 *  8/2012  Millman ................ A61B 34/71
                                                  606/1
8,380,319 B2    2/2013  Berger
(Continued)

*Primary Examiner* — Michael F Peffley
(74) *Attorney, Agent, or Firm* — Metrolex IP Law Group, PLLC (57) ABSTRACT

A surgical instrument according to an embodiment may include: a shaft; an end effector provided on a side of one end of the shaft; a housing including a base to which the other end of the shaft is connected, and a lid portion to cover the base; and a circuit board disposed on the base. The housing includes a press portion that presses the circuit board to the base to hold the circuit board.

17 Claims, 7 Drawing Sheets

(56) References Cited

U.S. PATENT DOCUMENTS

| | | | |
|---|---|---|---|
| 8,475,453 B2* | 7/2013 | Marczyk | A61B 18/1445 |
| | | | 606/51 |
| 9,307,986 B2* | 4/2016 | Hall | A61B 34/74 |
| 10,303,641 B2* | 5/2019 | Collins | A61B 90/90 |
| 2002/0032452 A1 | 3/2002 | Tierney et al. | |
| 2012/0110810 A1 | 5/2012 | Houser et al. | |
| 2014/0367445 A1* | 12/2014 | Ingmanson | A61B 17/07207 |
| | | | 227/175.2 |
| 2017/0079642 A1* | 3/2017 | Overmyer | H02P 6/14 |
| 2019/0223291 A1 | 7/2019 | Seow et al. | |

* cited by examiner

SURGICAL INSTRUMENT

CROSS REFERENCE TO RELATED APPLICATIONS

This application claims priority to Japanese Patent Application No. 2019-192618 filed on Oct. 23, 2019, the entire contents of which are incorporated herein by reference.

BACKGROUND

The disclosure may relate to a surgical instrument and may especially relate to a surgical instrument including a circuit board.

In a related art, there has been known a surgical instrument including a circuit board.

U.S. Patent Application Publication No. 2002/0032452 discloses a surgical instrument including a circuit board provided in a housing.

SUMMARY

In order to improve the assembling workability of the surgical instrument, a technology capable of easily attaching a circuit board to the housing may be desired.

An object of an embodiment of the disclosure may be to provide a surgical instrument that allows a circuit board to be easily attached.

A surgical instrument according to a first aspect of the disclosure may include: a shaft; an end effector provided on a side of one end of the shaft; a housing including a base to which the other end of the shaft is connected, and a lid portion to cover the base; and a circuit board disposed on the base. The housing includes a press portion that presses the circuit board to the base to hold the circuit board.

A surgical instrument according to a second aspect of the disclosure may include: a shaft; an end effector provided on a side of one end of the shaft; a housing including a base to which the other end of the shaft is connected, and a lid portion to cover the base; and a circuit board disposed on the base. The lid portion of the housing includes a press portion that presses the circuit board to the base to hold the circuit board.

A method of assembling a surgical instrument according to a third aspect of the disclosure may include: preparing a base to which one end of a shaft is connected wherein an end effector is provided on a side of the other end of the shaft and wherein a circuit board formed with a projection is disposed on the base, a lid portion to cover the base, a housing component configured to constitute a housing together with the base and the lid portion and including a press portion. The method of assembling the surgical instrument may further include: disposing the housing component in such a manner that the press portion of the housing component is in contact with the projection of the circuit board disposed on the base; sliding the housing component with respect to the base while sliding the press portion of the housing component in contact with the projection of the circuit board on the projection of the circuit board, so as to attach the housing component to the base; and attaching the lid portion of the housing to the base to which the housing component is attached.

DETAILED DESCRIPTION

Descriptions are provided hereinbelow for one or more embodiments based on the drawings. In the respective drawings referenced herein, the same constituents are designated by the same reference numerals and duplicate explanation concerning the same constituents is omitted. All of the drawings are provided to illustrate the respective examples only.

(Configuration of Robotic Surgical System)

A configuration of a robotic surgical system 100 according to an embodiment is described with reference to FIGS. 1 and 2.

Figure 1:
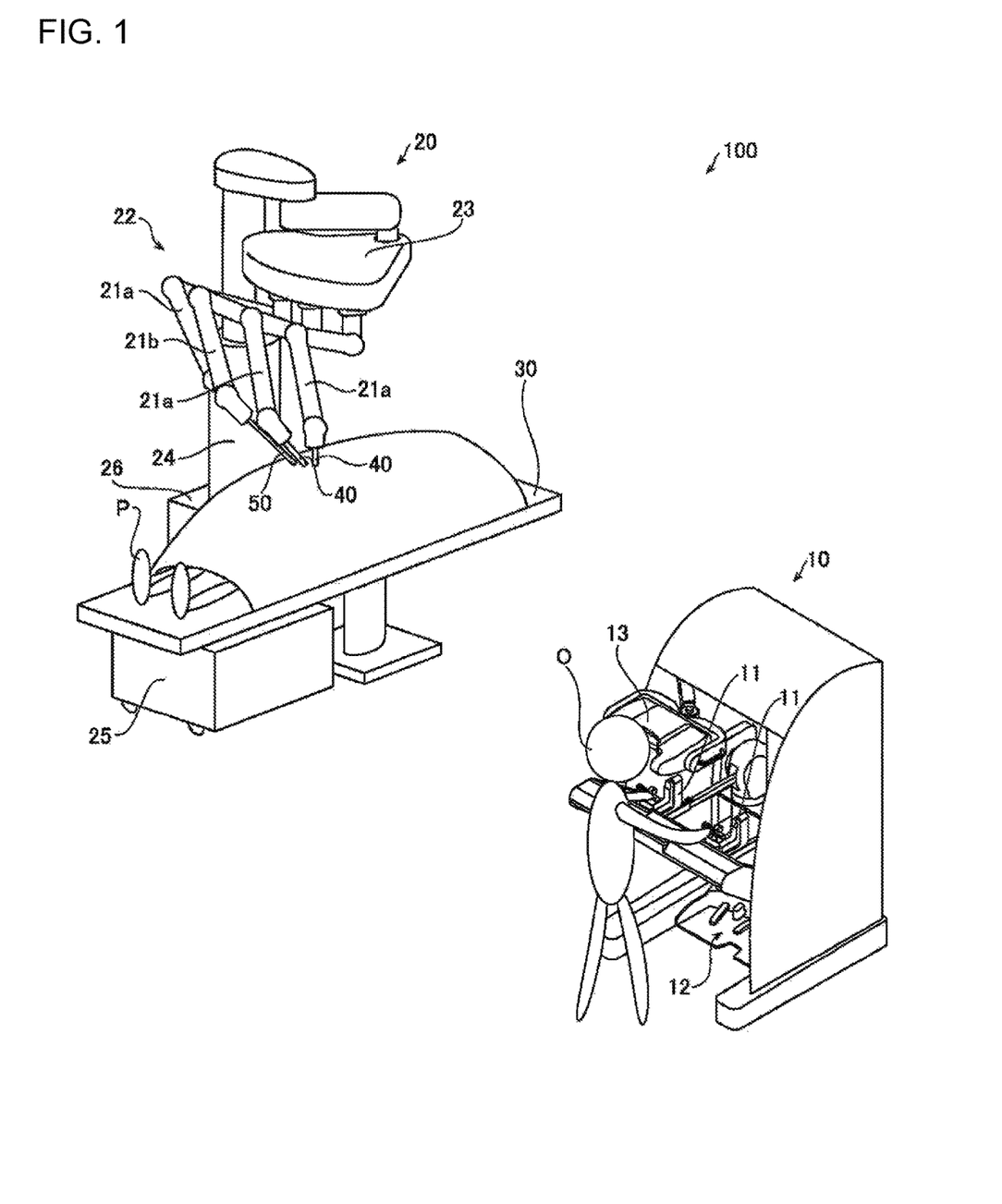
FIG. 1 is a diagram illustrating an overview of a robotic surgical system according to an embodiment.

As illustrated in FIG. 1, the robotic surgical system 100 includes a remote control apparatus 10 and a patient-side apparatus 20.

The remote control apparatus 10 is provided to remotely control medical equipment provided to the patient-side apparatus 20. When an operator O, as a surgeon, inputs an action mode instruction to be executed by the patient-side apparatus 20, to the remote control apparatus 10, the remote control apparatus 10 transmits the action mode instruction to the patient-side apparatus 20 through a controller 26. In response to the action mode instruction transmitted from the remote control apparatus 10, the patient-side apparatus 20 operates medical equipment such as surgical instruments 40, an endoscope 50, and the like, attached to robot arms 21a and 21b. This allows for minimally invasive surgery.

The patient-side apparatus 20 constitutes an interface to perform a surgery for a patient P. The patient-side apparatus 20 is positioned beside an operation table 30 on which the patient P is laid. The patient-side apparatus 20 includes plural robot arms 21a and 21b. One (21b) of the robot arms holds the endoscope 50 and the other robot arms 21a hold the surgical instruments 40. The robot arms 21a and 21b are commonly supported by a platform 23. Each of the robot arms 21a and 21b includes plural joints. Each joint includes a driver provided with a servo-motor and a position detector such as an encoder. The robot arms 21a and 21b are configured so that the medical equipment attached to each robot arm 21a and 21b is controlled by a driving signal given through the controller 26 and performs a desired movement.

The platform 23 is supported by a positioner 22 placed on the floor of an operation room. The positioner 22 includes a column 24 and a base 25. The column 24 includes an elevation shaft adjustable in the vertical direction. The base 25 includes wheels and is movable on the floor surface.

Figure 3:
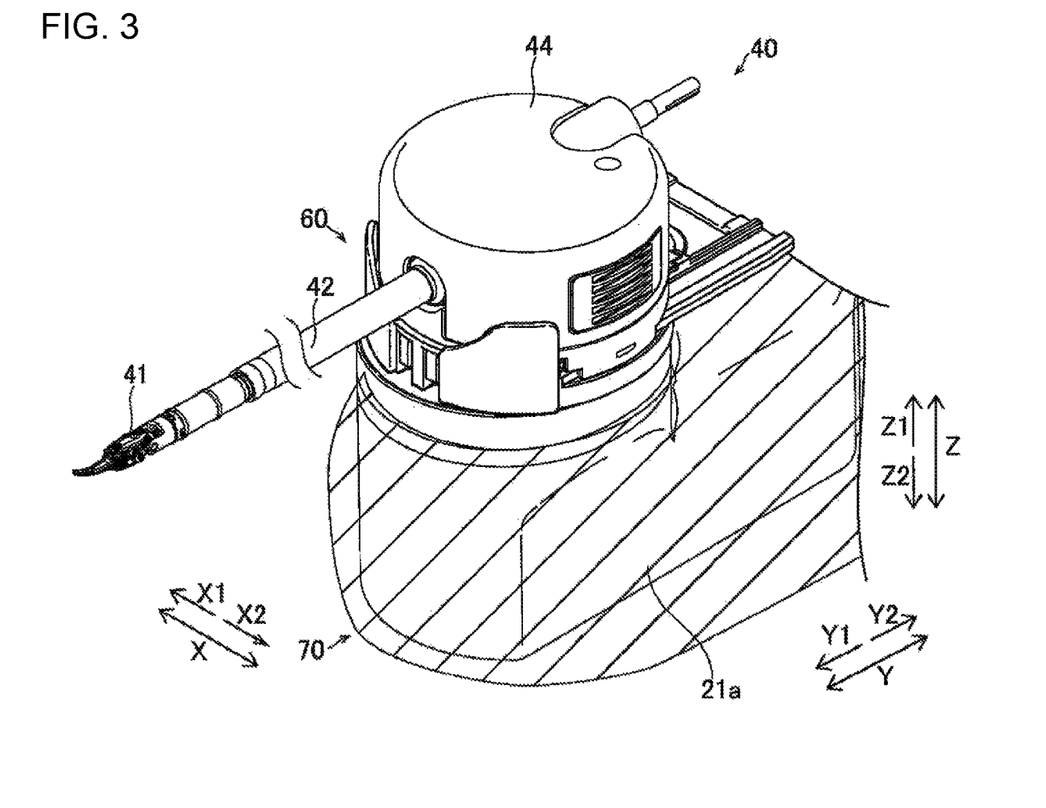
FIG. 3 is a diagram illustrating a perspective view of a state where a surgical instrument is attached to a robot arm through an adaptor according to an embodiment.

The surgical instruments 40 as the medical equipment is detachably attached to the distal ends of the robot arms 21a. The surgical instrument 40 is a surgical instrument that is detachably connected to the robot arm 21a of the robotic surgical system 100 through the adaptor 60, as illustrated in FIG. 3. The surgical instrument 40 includes an end effector 41, and an elongate shaft 42, wherein the end effector 41 is provided at one end of the shaft 42. The end effector 41 is grasping forceps, scissors, a hook, a high-frequency knife, a snare wire, a clamp, or a stapler, for example. The end effector 41 is not limited to those and can be various types of treatment tools. In surgeries using the patient-side apparatus 20, the robot arms 21a introduce the surgical instruments 40 into the body of the patient P through a cannula (trocar) placed on the body surface of the patient P. The end effectors 41 of the surgical instruments 40 are then located near the surgery site.

To the distal end of the robot arm 21b, the endoscope 50 as the medical equipment is detachably attached. The endoscope 50 captures an image in a body cavity of the patient P. The captured image is outputted to the remote control apparatus 10. The endoscope 50 is a 3D endoscope capable of capturing a three-dimensional image or a 2D endoscope. In surgeries using the patient-side apparatus 20, the robot arm 21b introduces the endoscope 50 into the body of the patient P through a trocar placed on the body surface of the patient P. The endoscope 50 is then located near the surgery site.

The remote control apparatus 10 constitutes the interface with the operator O. The remote control apparatus 10 is an apparatus that allows the operator O to operate the medical equipment attached to the robot arms 21a and 21b. Specifically, the remote control apparatus 10 is configured to transmit action mode instructions which are inputted by the operator O and are to be executed by the surgical instruments 40 and endoscope 50, to the patient-side apparatus 20 through the controller 26. The remote control apparatus 10 is installed beside the operation table 30 so that the operator O can see the condition of the patient P very well while operating the remote control apparatus 10, for example. The remote control apparatus 10 may be configured to transmit action mode instructions wirelessly and installed in a room different from the operation room where the operation table 30 is installed.

The action modes to be executed by the surgical instruments 40 include modes of actions to be taken by each surgical instrument 40 (a series of positions and postures) and actions to be executed by the function of each surgical instrument 40. When the surgical instrument 40 is a pair of grasping forceps, for example, the action modes to be executed by the surgical instrument 40 include roll and pitch positions of the wrist of the end effector 41 and actions to open and close the jaws. When the surgical instrument 40 is a high-frequency knife, the action modes to be executed by the surgical instrument 40 include vibration of the high-frequency knife, specifically, supply of current to the high-frequency knife. When the surgical instrument 40 is a snare wire, the action modes to be executed by the surgical instrument 40 include a capturing action and an action to release the captured object. Further the action modes may include an action to supply current to a bipolar or monopolar instrument to burn off the surgery site.

The action modes to be executed by the endoscope 50 include the position and posture of the tip of the endoscope 50 and setting of the zoom magnification, for example.

Figure 2:
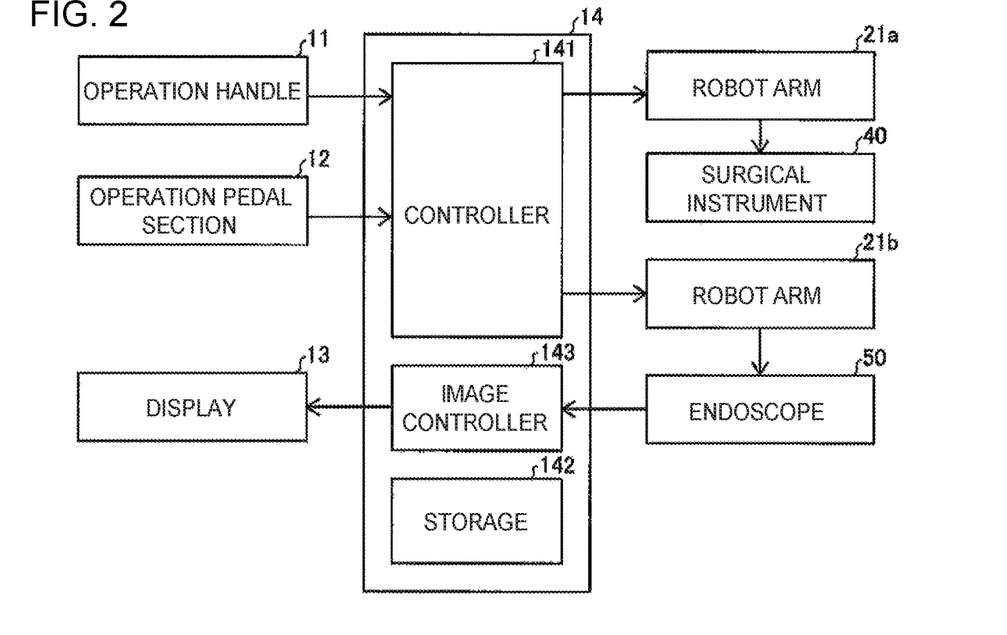
FIG. 2 is a block diagram illustrating a view of a control-related configuration of the robotic surgical system according to an embodiment.

As illustrated in FIGS. 1 and 2, the remote control apparatus 10 includes operation handles 11, an operation pedal section 12, a display 13, and a control apparatus 14.

The operation handles 11 are provided in order to remotely operate the medical equipment attached to the robot arms 21a and 21b. Specifically, the operation handles 11 accept operations by the operator O for operating the medical equipment (the surgical instruments 40 and endoscope 50). The operation handles 11 include two operation handles 11 arranged side by side in the horizontal direction. One of the two operation handles 11 is operated by the right hand of the operator O while the other operation handle 11 is operated by the left hand of the operator O.

The operation handles 11 extend from the rear side of the remote control apparatus 10 toward the front side. The operation handles 11 are configured to move in a predetermined three-dimensional operation region. Specifically, the operation handles 11 are configured so as to move up and down, right and left, and forward and rearward.

The remote control apparatus 10 and patient-side apparatus 20 constitute a master-slave system in terms of controlling movement of the robot arms 21a and robot arm 21b. The operation handles 11 constitute an operating section or an operating part on the master side in the master-slave system, and the robot arms 21a and 21b holding the medical equipment constitute an operating section or an operation part on the slave side. When the operator O operates the operation handles 11, the movement of one of the robot arms 21a or 21b is controlled so that the distal end portion (the end effector 41 of the surgical instrument 40) of the robot arm 21a or the distal end portion (the endoscope 50) of the robot arm 21b moves following the movement of the operation handles 11.

The patient-side apparatus 20 controls the movement of the robot arms 21a in accordance with the set motion scaling ratio. When the motion scaling ratio is set to ½, for example, the end effectors 41 of the surgical instruments 40 move ½ of the movement distance of the operation handles 11. This allows for precise fine surgery.

The operation pedal section 12 or an operation pedal unit includes plural pedals to execute medical equipment-related functions. The plural pedals include a coagulation pedal, a cutting pedal, a camera pedal, and a clutch pedal. The plural pedals are operated by a foot of the operator O.

The coagulation pedal enables the surgical instrument 40 to coagulate a surgery site. Specifically, when the coagulation pedal is operated, voltage for coagulation is applied to the surgical instrument 40 to coagulate a surgery site. The cutting pedal enables the surgical instrument 40 to cut a surgery site. Specifically, the cutting pedal is operated to apply voltage for cutting to the surgical instrument 40 and cut a surgery site.

The camera pedal is used to control the position and orientation of the endoscope 50 that captures images within the body cavity. Specifically, the camera pedal enables operation of the endoscope 50 by the operation handles 11. That is, the position and orientation of the endoscope 50 are controllable by the operation handles 11 while the camera pedal is being pressed. The endoscope 50 is controlled by using both of the right and left operation handles 11, for example. Specifically, when the operator O rotates the right and left operation handles 11 about the middle point between the right and left operation handles 11, the endoscope 50 is rotated. When the operator O presses the right and left operation handles 11 together, the endoscope 50 goes forward into the body cavity. When the operator O pulls the right and left operation handles 11 together, the endoscope 50 goes back. When the operator O moves the right and left operation handles 11 together up, down, right, or left, the endoscope 50 moves up, down, right, or left, respectively.

The clutch pedal is used to temporarily disconnect operation-related connection between the operation handles 11 and the robot arms 21a to stop movement of the surgical instruments 40. Specifically, when the clutch pedal is being pressed, the robot arms 21a of the patient-side apparatus 20 do not work even if the operation handles 11 are operated. For example, when the operation handles 11 are operated and moved to the edge of the range of movement, the operator O operates the clutch pedal to temporarily disconnect the operation-related connection and then returns the operation handles 11 to the center of the range of movement. When the operator O stops operating the clutch pedal, the operation handles 11 are again connected to the robot arms 21a. The operator O restarts the operation for the operation handles 11 around the center thereof.

The display 13 (a display unit or display device) is configured to display images captured by the endoscope 50. The display 13 includes a scope type display or a non-scope type display. The scope type display is a display that the operator O looks into. The non-scope type display is a display like an open-type display that includes a flat screen and the operator O is able to see without looking into, such as normal displays for personal computers.

When the scope type display is attached, the scope type display displays 3D images captured by the endoscope 50 attached to the robot arm 21b of the patient-side apparatus 20. When the non-scope type display is attached, the non-scope type display also displays 3D images captured by the endoscope 50 provided for the patient-side apparatus 20. The non-scope type display may display 2D images captured by the endoscope 50 provided for the patient-side apparatus 20.

As illustrated in FIG. 2, the control apparatus 14 includes a controller 141, a storage 142, and an image controller 143, for example. The controller 141 includes a calculator such as a CPU. The storage 142 includes a memory, such as a ROM and a RAM. The control apparatus 14 may be composed of a single controller performing centralized control or may be composed of plural controllers that perform decentralized control in cooperation with each other. The controller 141 determines whether an action mode instruction inputted by the operation handles 11 is to be executed by the robot arms 21a or to be executed by the endoscope 50, depending on the state of the operation pedal section 12. When determining that the action mode instruction inputted by the operation handles 11 is to be executed by any one of the surgical instruments 40, the controller 141 transmits the action mode instruction to the corresponding robot arm 21a. The robot arm 21a is thereby driven for controlling movement of the surgical instrument 40 attached to the robot arm 21a.

When determining that the action mode instruction inputted by the operation handles 11 is to be executed by the endoscope 50, the controller 141 transmits the action mode instruction to the robot arm 21b. The robot arm 21b is thereby driven for control of movement of the endoscope 50 attached to the robot arm 21b.

The storage 142 stores control programs corresponding to the types of the surgical instrument 40, for example. The controller 141 reads the stored control programs according to the types of the attached surgical instruments 40. The action mode instructions from the operation handles 11 and/or the operation pedal section 12 of the remote control apparatus 10 thereby cause the respective surgical instruments 40 to perform proper movements.

The image controller 143 transmits images acquired by the endoscope 50 to the display 13. The image controller 143 performs processing and modifying the images when needed.

(Configurations of Adaptor and Surgical Instrument)

With reference to FIGS. 3 to 7, the configuration of the surgical instrument 40 according to an embodiment is described.

The surgical instrument 40 is the surgical instrument that is attached to the robot arm 21a of the robotic surgical system 100, as illustrated in FIG. 3. The robot arm 21a is used in a clean area and is thus covered with the drape 70. In operation rooms, clean technique is used in order to prevent surgical incision sites and medical equipment from being contaminated by pathogen, foreign matters, or the like. The clean technique defines a clean area and a contaminated area, which is other than the clean area. The surgery sites are located in the clean area. Members of the surgical team, including the operator O, make sure that only sterile objects are placed in the clean area during surgery and perform sterilization for an object which is to be moved to the clean area from the contaminated area. Similarly, when the members of the surgical team including the operator O place their hands in the contaminated area, the members sterilize their hands before directly touching objects located in the clean area. Instruments used in the clean area are sterilized or are covered with sterile drape 70.

The drape 70 is arranged between the robot arm 21a and the surgical instrument 40. Specifically, the drape 70 is arranged between the adaptor 60 and the robot arm 21a. Further, the drape 70 is arranged between the robot arm 21b and the endoscope 50. The adaptor 60 is attached to the robot arm 21a while putting the drape 70 between the adaptor 60 and the robot arm 21a. Specifically, the adaptor 60 is a drape adaptor that puts the drape 70 between the adaptor 60 and the robot arm 21a. The drape 70 is thus able to be mounted through the adaptor 60. The surgical instrument 40 is attached to the adaptor 60 that is attached to the robot arm 21a with the drape 70 interposed therebetween. The robot arm 21a transmits driving force to the surgical instrument 40 through the adaptor 60 to drive the end effector 41 of the surgical instrument 40.

Figure 4:
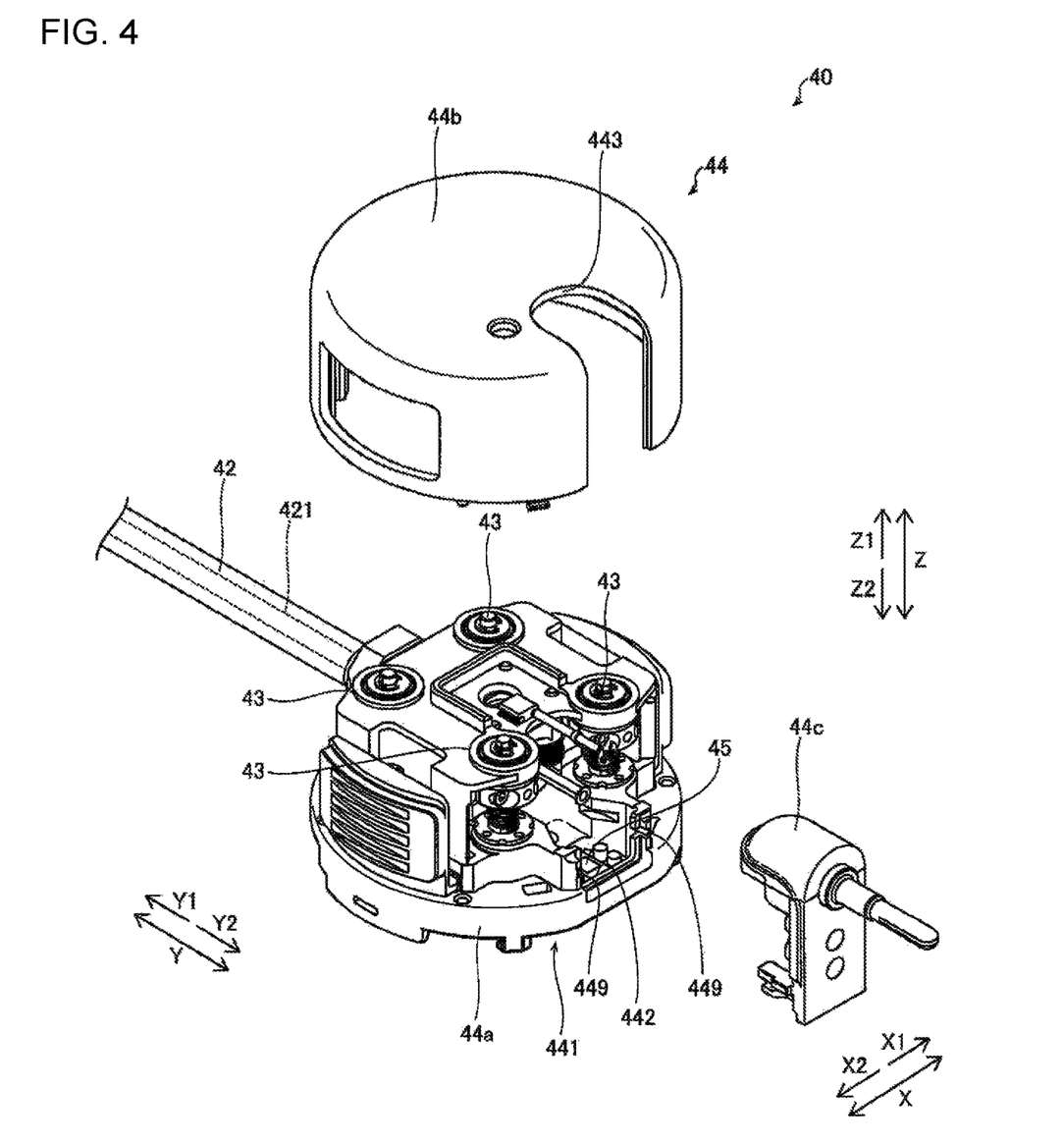
FIG. 4 is a diagram illustrating a perspective view of a state where a lid portion and a housing component are detached from a base according to an embodiment.

As illustrated in FIG. 4, the surgical instrument 40 includes the plural driven members 43, a housing 44, and a circuit board 45.

The driven members 43 are driven to be rotated to drive the end effector 41. Specifically, the end effector 41 is connected to one end (an end portion on the Y1 side, a first end) of the shaft 42, and the other end (an end portion on the Y2 side, a second end) of the shaft 42 is connected to a base 44a (described later) of the housing 44. The driven members 43 are rotatably provided on the base 44a. One or more of the driven members 43 are connected to the end effector 41 with wires 421 inserted through the shaft 42. Specifically, end portions of the wires 421 operating the end effector 41 are connected to the one or more driven members 43, respectively. When the one or more of the driven members 43 are rotated, the wires 421 are drawn to drive the end effector 41. In the housing 44, one or more of the driven members 43 are connected to the shaft 42 through a gear(s)

such that when the one or more of the driven members 43 are rotated, the shaft 42 is rotated.

For example, four driven members 43 are provided. The shaft 42 is rotated by the rotation of one of the driven members 43. The end effector 41 is driven by the rotations of the other three driven members 43. The four driven members 43 are arranged in two rows (columns) in the X direction and two columns (rows) in the Y direction. The driven members 43 are provided in the housing 44.

The housing 44 is configured to form a housing (or a casing) of the surgical instrument 40. Specifically, the housing 44 includes the base 44a including an adaptor attachment surface 441, a lid portion 44b, and a housing component 44c. The base 44a is formed with the adaptor attachment surface 441 on the Z2 side of the base 44a. The driven members 43 are rotatably provided on the base 44a. To the base 44a, the other end of the shaft 42 is connected. The base 44a includes a recess portion 442 in which the circuit board 45 is to be provided. The recess portion 442 is recessed toward the Z2 direction. The recess portion 442 is provided on a portion of the base 44a on the Y2 side. Specifically, the recess portion 442 is provided on an end portion of the base 44a on the Y2 side.

The lid portion 44b is configured to cover the base 44a. Specifically, the lid portion 44b is configured to cover the based from the Z1 side of the base 44a. The lid portion 44b is also configured to detachably attached to the base 44a. The lid portion 44b is formed with a removed portion 443 (an opening or a cutout) in which the housing component 44c is to be disposed. The removed portion 443 is provided on a portion of the lid portion 44b on the Y2 side.

The housing component 44c is configured to constitute the housing 44 together with the base 44a and the lid portion 44b. Specifically, the housing component 44c is configured to form a part of the lid portion 44b. The housing component 44c is configured to be attached to the base 44a by being slid in the Y1 direction (the slide attachment direction) with respect to the base 44a. Accordingly, the housing component 44c can be easily attached to the base 44a. Note that the base 44a, the lid portion 44b, and the housing component 44c may be referred to as housing members. The lid portion 44b and the housing component 44c covering the base 44a may be referred to as cover members or may be referred to as lid members.

Figure 5:
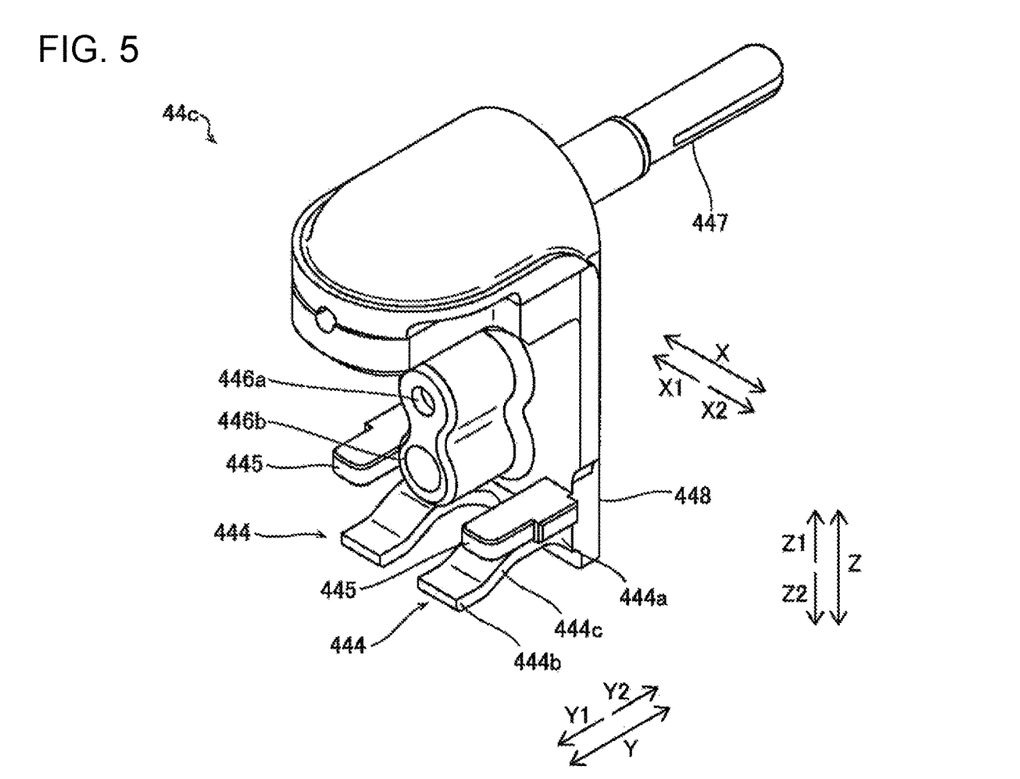
FIG. 5 is a diagram illustrating a perspective view of the housing component according to an embodiment.
Figure 7:
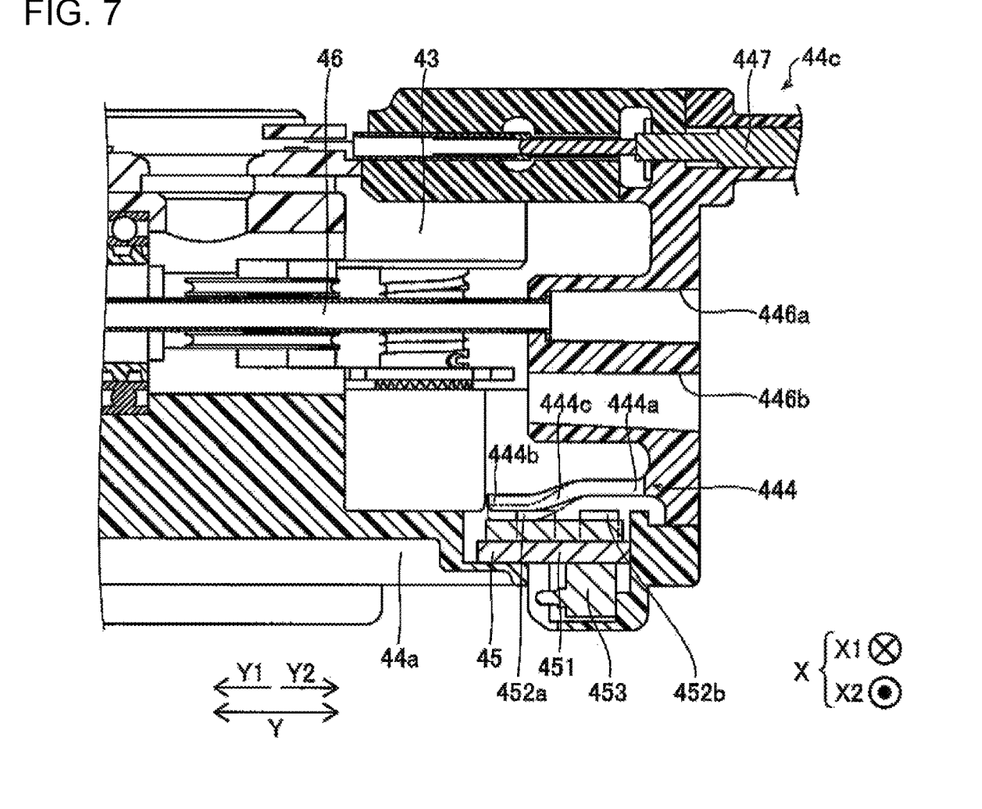
FIG. 7 is a diagram illustrating a cross sectional view of the surgical instrument according to an embodiment.

As illustrated in FIGS. 5 and 7, the housing component 44c includes a pair of press portions 444, a pair of engagement projections 445, cleaning liquid supply ports 446a and 446b (flash ports), and an electrode 447.

Here, in an embodiment, the pair of press portions 444 is configured to press the circuit board 45 to the base 44a so as to hold the circuit board 45. With this configuration, the circuit board 45 is attached to the base 44a by means of the pair of press portions 444. Therefore, compared to a case where the circuit board 45 is attached to the base 44a by press fitting, the force required to attach the circuit board 45 to the base 44a can be reduced. As a result, the circuit board 45 can be easily attached. Further, unlike a case where the circuit board 45 is attached to the base 44a by means of a bolt(s), no bolts, which may be loosened due to vibrations or the like are needed to attach the circuit board 45 to the base 44a, since the circuit board 45 is attached to the base 44a by means of the pair of press portions 444. In an embodiment, the pair of press portions 444 is provided at the housing component 44c. Therefore, unlike a case where the pair of press portions 444 is provided at the base 44a or the lid portion 44b, the pair of press portions 444 can be easily provided.

The press portions 444 are provided to extend in the Y direction. The press portions 444 are provided to extend substantially in parallel to each other. The press portions 444 are opposed to each other in the X direction. The press portions 444 are provided away from each other in the X direction by a predetermined distance. The press portions 444 press both end portions, in the X direction, of the circuit board 45, so as to fix the circuit board 45. That is, one of the press portions 444 on the X1 side presses a portion of the circuit board 45 on the X1 side to fix the X1 side portion of the circuit board 45. The other of the press portions 444 on the X2 side presses a portion of the circuit board 45 on the X2 side to fix the X2 side portion of the circuit board 45.

Each of the press portions 444 is configured to be elastically deformed (resiliently deformed) to press the circuit board 45 to the base 44a so as to hold the circuit board 45. Accordingly, the pressing force (biasing force) can be applied to the circuit board 45 by the elastic deformation (resilient deformation), so that an appropriate amount of the pressing force can be applied to the circuit board 45. Specifically, each of the press portions 444 is a pressing arm which is elastically deformable. With this configuration, the press portions 444 can be formed with a simple configuration. Thus, even when the press portions 444 are provided, it is possible to prevent the structure from becoming complicated. Each of the press portions 444 is provided to protrude from a main body 448 of the housing component 44c in the Y1 direction. Note that, in FIG. 7, for ease of understanding, the press portions 444 before the elastic deformation are illustrated by the chain double-dashed line, and the press portions 444 after the elastic deformation are illustrated by the solid line.

Each of the press portions 444 includes a fixed end portion 444a, a distal end portion 444b as a free end, and a connection portion 444c. The fixed end portion 444a of the press portion 444 is provided on the Y2 side of the press portion 444 and is fixed to the housing component 44c. The distal end portion 444b of the press portion is provided on the Y1 side of the press portion 444 and is not fixed. The distal end portion 444b is chamfered. With this, it is possible to suppress the occurrence of damage due to the distal end portions 444b of the press portions 444 when the press portions 444 press the circuit board 45. When the press portions 444 are slid while pressing the circuit board 45, the chamfered distal end portions 444b of the press portions 444 can smoothly press the circuit board 45 without being caught by the projections 452a and 452b (described later) of the circuit board 45. Specifically, a corner portion of the distal end portion 444b on the Z2 side is chamfered in an arc shape.

The press portions 444 are made of an insulating material. Accordingly, it is possible to easily prevent the press portions 444 from electrically affecting the circuit board 45, unlike a case where the press portions 444 are made of a conductive material. Specifically, the press portions 444 are made of an insulating resin material.

The connection portion 444c is provided to connect the fixed end portion 444a and the distal end portion 444b. The connection portion 444c is provided to extend along the Y direction. The connection portion 444c is formed with bent portions. Specifically, the connection portion 444c is provided so as to be bent from the Z1 side to the Z2 side. The connection portion 444c is configured to be elastically deformable in the Z direction.

The pair of engagement projections 445 is configured to be engaged with the base 44a. Specifically, the pair of engagement projections 445 is configured to be engaged with the pair of engagement recesses 449 (see FIG. 4), respectively. With the pair of engagement projections 445 being engaged with the pair of engagement recesses 449, the housing component 44*c* is connected to the base 44*a* so as not to come off the base 44*a* in the Z direction. The engagement projections 445 are provided to extend in the Y direction. The engagement projections 445 are provided to extend substantially in parallel to each other. The engagement projections 445 are opposed to each other in the X direction. The engagement projections 445 are provided away from each other in the X direction by a predetermined distance. The pair of engagement projections 445 is provided on the Z1 side with respect to the pair of press portions 444.

The cleaning liquid supply ports 446*a* and 446*b* are provided to supply a cleaning liquid (such as water or the like). That is, in an embodiment, the press portions 444 are provided to the housing component 44*c* to which the cleaning liquid supply ports 446*a* and 446*b* are provided. With this configuration, the press portions 444 and the cleaning liquid supply ports 446*a* and 446*b* can be provided in the common housing component 44*c*, so that the complication of the structure can be suppressed as compared with a case where the press portions 444 and the cleaning liquid supply ports 446*a* and 446*b* are provided in separate members, respectively.

The cleaning liquid supply ports 446*a* and 446*b* are provided to penetrate through the housing component 44*c* in the Y direction. The cleaning liquid supply ports 446*a* and 446*b* are arranged in the Z direction. The cleaning liquid supply port 446*a* on the Z1 side is provided to supply the cleaning liquid to the inside of the shaft 42. Specifically, the cleaning liquid supply port 446*a* is connected to the inside of the shaft 42 through a cleaning liquid tube 46 (see FIG. 7). The cleaning liquid supply ports 446*b* on the Z2 side is provided to supply the cleaning liquid to the inside of the housing 44. Specifically, the Y1 side end of the cleaning liquid supply port 446*b* is connected to the inside of the housing 44.

The electrode 447 is provided for supplying electric power to the end effector 41. The housing component 44*c* functions as an electrode holding member that holds the electrode 447. With this configuration, the press portions 444 and the electrode 447 can be provided in the common housing component 44*c*, so that the complication of the structure can be suppressed as compared with a case where the press portions 444 and the electrode 447 are provided in separate members, respectively.

The electrode 447 is configured to be connected to a power supply source (not illustrated). In an embodiment, the end effector 41 is configured to generate heat by using the electric power supplied from the electric power supply source via the electrode 447.

Figure 6:
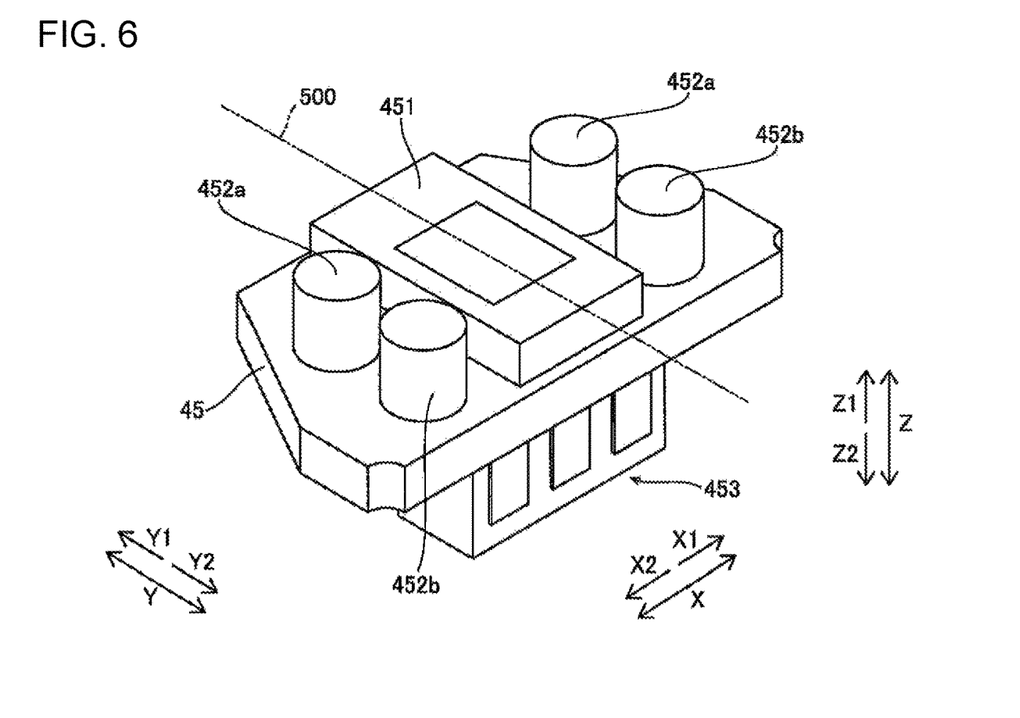
FIG. 6 is a diagram illustrating a perspective view of a circuit board according to an embodiment.

As illustrated in FIGS. 6 and 7, the circuit board 45 is disposed in the recess portion 442 of the base 44*a*. The circuit board 45 is a memory board. With this configuration, the circuit board 45, which is the memory board, can be easily attached to the base 44*a* by means of the pair of press portions 444. In the memory of the circuit board 45, information about the surgical instrument 40, such as the type of the surgical instrument 40, the number of times the surgical instrument 40 has been used, and the like, are stored, for example.

The circuit board 45 is provided with a circuit portion 451, plural projections 452*a* and 452*b*, and an electrode array 453. The projections 452*a* and 452*b* are examples of a "first projection" and a "second projection" in the disclosure, respectively.

The circuit portion 451 is provided on the Z1 side surface of the circuit board 45. The circuit portion 451 includes, for example, electronic components such as ROM (Read Only Memory) and/or the like.

The projections 452*a* and 452*b* protrude from the Z1 side surface of the circuit board 45 toward the side of the press portions 444 (in the Z1 direction). The projections 452*a* and 452*b* are configured to be pressed by the press portions 444. With this, the circuit board 45 can be pressed via the projections 452*a* and 452*b*. Thus, unlike a case where the circuit board 45 is directly pressed, it is possible to prevent the pressing load from being directly applied to the circuit board 45.

The projections 452*a* and 452*b* are arranged at positions symmetrical with respect to the center line 500 of the circuit board 45 in the X direction. With this, the circuit board 45 can be pressed evenly, since the circuit board 45 can be pressed through the plural projections 452*a* and 452*b* at positions symmetrical with respect to the center line 500. As a result, the circuit board 45 is stably attached to the base 44*a*.

The plural projections 452*a* and 452*b* are provided such that the circuit portion 451 of the circuit board 45 is provided between the projections 452*a* and 452*b*. With this, the plural projections 452*a* and 452*b* can be provided at positions not overlapping with the circuit portion 451, and the circuit board 45 can be pressed at the positions not overlapping with the circuit portion 451 at the plural projections 452*a* and 452*b*.

Each of the projections 452*a* and 452*b* is formed in a cylindrical shape (circular column shape). The projections 452*a* and 452*b* are provided to extend along the Z direction. The Z1 side end of each of the projections 452*a* and 452*b* is pressed by the press portion 444 at a position higher than the circuit portion 451. The Z2 side end of each of the projections 452*a* and 452*b* are bonded to the Z1 side surface of the circuit board 45 by soldering.

The number of the projections 452*a* provided are two. The number of the projections 452*b* provided are two. The two projections 452*a* are provided in the X1 side and the X2 side of the circuit board 45, respectively. The two projections 452*b* are provided in the X1 side and the X2 side of the circuit board 45, respectively. On each of the X1 side and the X2 side, one projection 452*a* and one projection 452*b* are arranged in the Y direction.

The projections 452*a* are provided on the Y1 side (a downstream side of the slide attachment direction of the housing component 44*c*). The projections 452*b* are provided on the Y2 side (an upstream side of the slide attachment direction of the housing component 44*c*). With this configuration, upon slide attachment of the housing component 44*c* to the base 44*a*, the press portions 444 can be slid on the projections 452*a* and 452*b*, so that the slide attachment of the housing component 44*c* can be easily performed.

Specifically, the projections 452*b* are provided at positions where they are pressed by the press portions 444 when the slide attachment of the housing component 44*c* is started. Further, the projections 452*a* are provided at positions where they are pressed by the press portions 444 when the slide attachment of the housing component 44*c* is completed (ended). With this configuration, the press portions 444 can be slid on the projections 452*a* and 452*b* from the start to the completion of the slide attachment of the housing component 44c. Therefore, the slide attachment of the housing component 44c can be performed more easily.

The electrode array 453 is provided at the Z2 side surface of the circuit board 45. The electrode array 453 is electrically connected to an electrode array of the robot arm 21a through an electrode array of the adaptor 60. Accordingly, the information stored in the circuit board 45 can be grasped on the robot arm 21a side.

(Assembling Surgical Instrument)

With reference to FIGS. 8 to 11, assembling of the surgical instrument 40 according to an embodiment is described.

Figure 8:
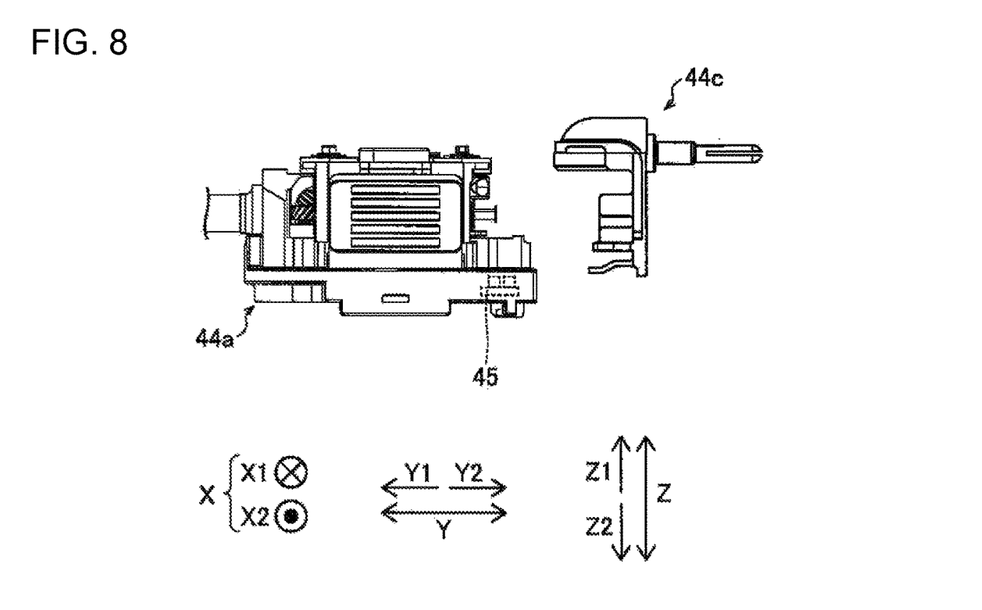
FIG. 8 is a diagram illustrating a first explanatory view for explaining attachment of the housing component to the base according to an embodiment.
Figure 9:
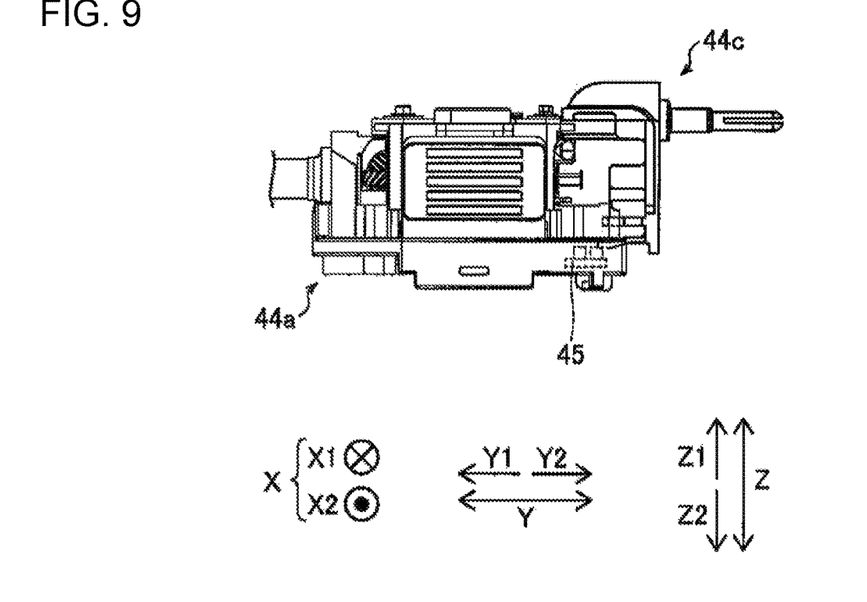
FIG. 9 is a diagram illustrating a second explanatory view for explaining the attachment of the housing component to the base according to an embodiment.

As illustrated in FIGS. 8 to 11, the attachment of the housing component 44c to the base 44a can be performed by moving the housing component 44c with respect to the base 44a in the Y1 direction. Specifically, first, as illustrated in FIG. 8, the base 44a and the housing component 44c are prepared. Then, as illustrated in FIG. 9, the housing component 44c is disposed such that the press portions 444 of the housing component 44c and the projections 452b of the circuit board 45 are in contact with each other. At this time, the press portions 444 are elastically deformed toward the Z1 side and thus press the circuit board 45 toward the Z2 side by the elastic force (restoring force). Note that upon the start of the attachment of the housing component 44c, the press portions 444 press only the projections 452b among the projections 452a and 452b.

Figure 10:
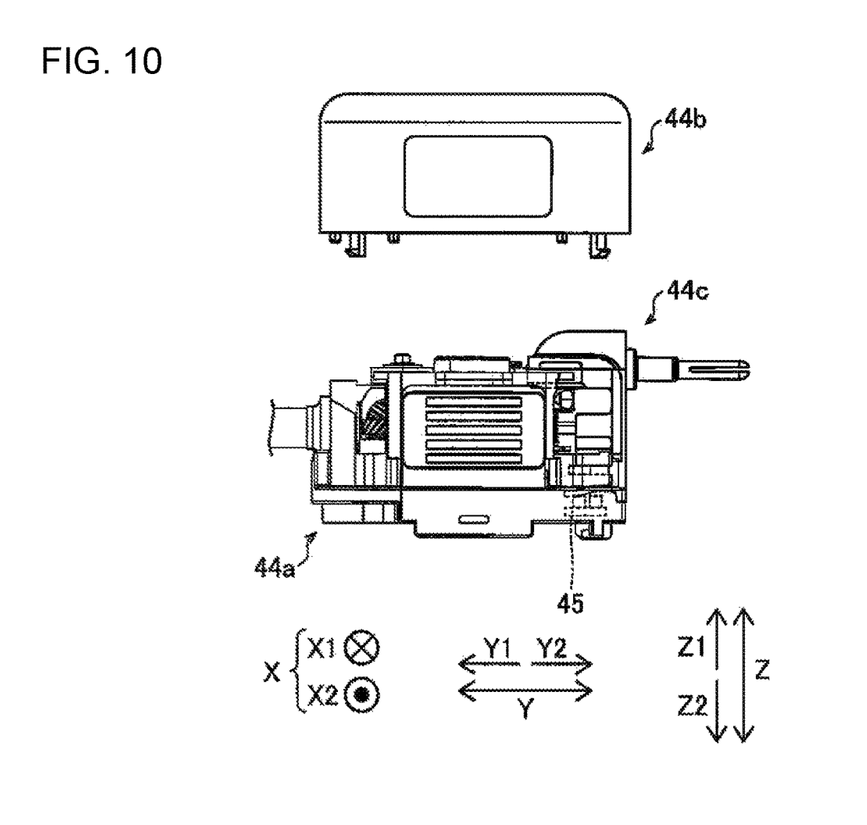
FIG. 10 is a diagram illustrating a first explanatory view for explaining attachment of the lid portion to the base according to an embodiment.

Then, when the housing component 44c is slid in the Y1 direction, the housing component 44c is attached to the base 44a, as illustrated in FIG. 10. In the slide attachment of the housing component 44c, the press portions 444 are slid on the projections 452a and 452b while being elastically deformed toward the Z1 side. When the attachment of the housing component 44c is completed, the the press portions 444 press only the projections 452a among the projections 452a and 452b. Also, the pair of engagement projections 445 is engaged with the pair of engagement recesses 449, respectively.

Figure 11:
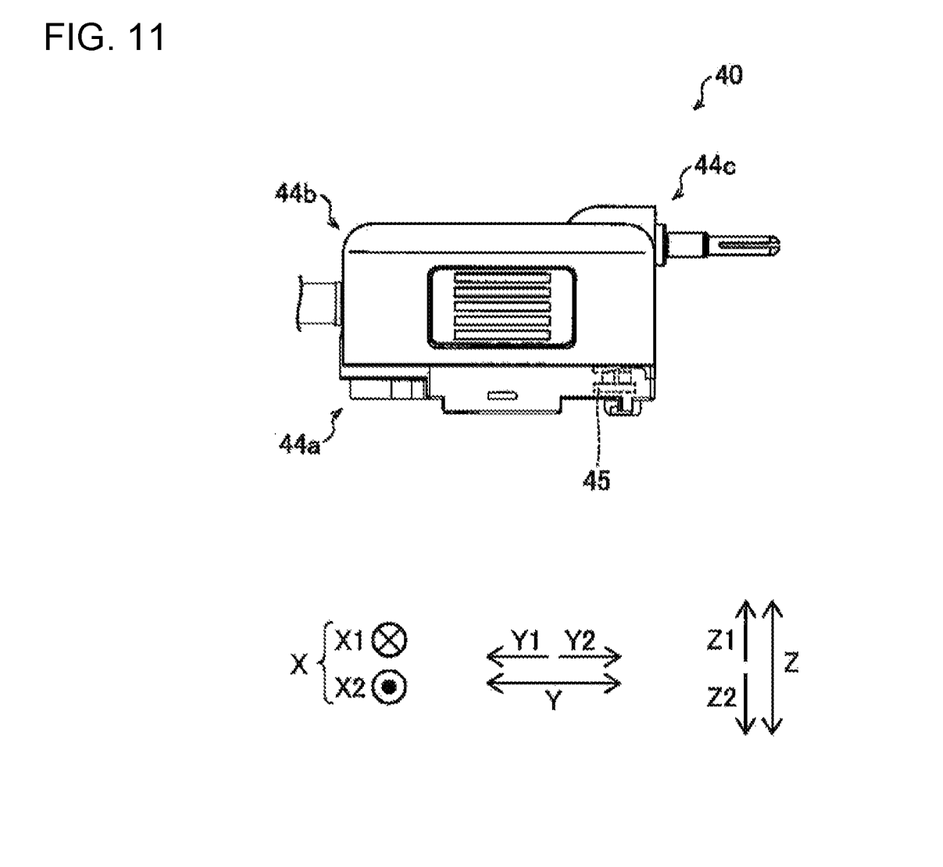
FIG. 11 is a diagram illustrating a second explanatory view for explaining the attachment of the lid portion to the base according to an embodiment.

Finally, as illustrated in FIGS. 10 and 11, the lid portion 44b is moved in the Z2 direction with respect to the base 44a, and is thus attached to the base 44a to which the housing component 44c is attached. In this way, the surgical instrument 40 is assembled.

(Modifications)

It should be understood that one or more embodiments described above are illustrated by way of example in every respect and not limit the invention. The scope of the invention is defined not by the above-described one or more embodiments, but by the scope of claims, and includes all modifications (variations) within equivalent meaning and scope to those of the claims.

For example, in an embodiment described above, the housing component is provided with the press portions. However, the disclosure is not limited to this. In the disclosure, a press portion may be provided to a base or a lid portion of a housing.

Further, in an embodiment described above, the housing component functions as the electrode holding member. However, the disclosure is not limited this. In the disclosure, a housing component do not necessarily have to hold an electrode.

In an embodiment described above, the housing component is provided with the cleaning liquid supply ports. However, the disclosure is not limited to this. In the disclosure, a housing component do not necessarily have to include a cleaning liquid supply port.

In an embodiment described above, the pair (two) of press portions is provided. However, the disclosure is not limited to this. In the disclosure, the number of a press portion(s) may be one or more than two.

In an embodiment described above, the four projections are provided to the circuit board. However, the disclosure is not limited to this. In the disclosure, one projection may be provided to a circuit board or plural projections (other than four) may be provided to the circuit board. Further, in the disclosure, the shape of each of the projections is not limited to the circular column shape.

In an embodiment described above, the plural projections are provided at the positions symmetrical with respect to the center line of the circuit board. However, the disclosure is not limited to this. In the disclosure, plural projections do not necessarily have to be provided at positions symmetrical with respect to a center line of a circuit board.

In an embodiment described above, the plural projections are provided such that the circuit portion is provided between the plural projections. However, the disclosure is not limited to this. In the disclosure, plural projections may be provided on one side on a circuit board with respect to a circuit portion.

In an embodiment described above, the plural projections include: the projections (first projections) to be pressed upon the start of the slide attachment of the housing component; and the projections (second projections) to be pressed upon the completion of the slide attachment of the housing component. However, the disclosure is not limited to this. In the disclosure, one projection may be provided which is pressed from a start to a completion of slide attachment of a housing component.

In an embodiment described above, the circuit board is the memory circuit. However, the disclosure is not limited to this. In the disclosure, a circuit board may be a circuit board other than a memory board.

The invention claimed is:

1. A surgical instrument comprising:
   a shaft;
   an end effector provided on a side of one end of the shaft;
   a housing including a base to which the other end of the shaft is connected, and a lid portion to cover the base; and
   a circuit board provided on the base, wherein
   the housing includes a press portion that presses the circuit board to the base to hold the circuit board,
   the press portion comprises a pressing arm configured to be elastically deformed to press the circuit board to the base so as to hold the circuit board, and
   the pressing arm includes a fixed end portion, a distal end portion as a free end portion, and a connection portion connecting the fixed end portion and the distal end portion.

2. The surgical instrument according to claim 1, wherein the circuit board is provided with a projection protruded from a surface of the circuit board toward the press portion and being configured to be pressed by the press portion.

3. The surgical instrument according to claim 2, wherein the projection comprises plural projections, and
   the plural projections are provided at positions symmetrical with respect to a center line of the circuit board.

4. The surgical instrument according to claim 2, wherein the projection comprises plural projections, and
   the plural projections are provided on both sides with respect to a circuit portion on the circuit board.

5. The surgical instrument according to claim 1, wherein the press portion is provided to a housing component configured to constitute the housing together with the base and the lid portion.

6. The surgical instrument according to claim 5, wherein the housing component is attached to the base by being slid with respect to the base.

7. The surgical instrument according to claim 6, wherein the circuit board is provided with a projection protruded from a surface of the circuit board toward the press portion and configured to be pressed by the press portion, and the projection comprises: a first projection provided on a downstream side of a direction of slide attachment of the housing component; and a second projection provided on an upstream side of the slide attachment direction of the housing component.

8. The surgical instrument according to claim 7, wherein the second projection is provided at a position to be pressed by the press portion upon a start of the slide attachment of the housing component, and the first projection is provided at a position to be pressed by the press portion upon a completion of the slide attachment of the housing component.

9. The surgical instrument according to claim 6, wherein the housing component includes an engagement projection extending in the slide attachment direction, the base includes an engagement recess to which the engagement projection is to be engaged.

10. The surgical instrument according to claim 5, wherein the housing component is configured to be an electrode holding member that holds an electrode.

11. The surgical instrument according to claim 5, wherein the housing component is provided with a cleaning liquid supply port to supply a cleaning liquid.

12. The surgical instrument according to claim 1, wherein the connection portion of the pressing arm is bent toward the circuit board.

13. The surgical instrument according to claim 1, wherein the distal end portion of the pressing arm is chamfered.

14. The surgical instrument according to claim 1, wherein the press portion is formed of an insulating material.

15. The surgical instrument according to claim 1, wherein the circuit board is a memory board.

16. A method of assembling a surgical instrument, comprising:

preparing a base to which one end of a shaft is connected wherein an end effector is provided on a side of the other end of the shaft and wherein a circuit board formed with a projection is disposed on the base, a lid portion to cover the base, a housing component configured to constitute a housing together with the base and the lid portion wherein the housing component includes a press portion including a pressing arm configured to be elastically deformed to press the circuit board to the base so as to hold the circuit board, wherein the pressing arm includes a fixed end portion, a distal end portion as a free end portion, and a connection portion connecting the fixed end portion and the distal end portion;

disposing the housing component in such a manner that the press portion of the housing component is in contact with the projection of the circuit board disposed on the base;

sliding the housing component with respect to the base while sliding the press portion of the housing component in contact with the projection of the circuit board on the projection of the circuit board, so as to attach the housing component to the base; and attaching the lid portion of the housing to the base to which the housing component is attached.

17. A surgical instrument comprising:

a shaft;

an end effector provided on a side of one end of the shaft;

a housing including a base to which the other end of the shaft is connected, a lid portion to cover the base, and a housing component configured to be attached to the base by being slid with respect to the base so as to constitute the housing together with the base and the lid portion; and a circuit board provided on the base, wherein the housing component includes a press portion that presses the circuit board to the base to hold the circuit board, the circuit board is provided with a projection protruded from a surface of the circuit board toward the press portion and being configured to be pressed by the press portion, and the projection comprises: a first projection provided on a downstream side of a direction of slide attachment of the housing component; and a second projection provided on an upstream side of the slide attachment direction of the housing component.

\* \* \* \* \*